United States Patent [19]

Kordes et al.

[11] Patent Number: Plant 5,846

[45] Date of Patent: Jan. 6, 1987

[54] ROSE PLANT KORLINGO

[75] Inventors: Reimer Kordes; Werner Kordes; Hermann Kordes, all of Klein Offenseth-Sparrieshoop, Fed. Rep. of Germany

[73] Assignee: Jackson & Perkins Company, Medford, Oreg.

[21] Appl. No.: 730,073

[22] Filed: May 3, 1985

[51] Int. Cl.[4] ..... A01H 5/00

[52] U.S. Cl. ..... Plt./20

[58] Field of Search ..... Plt./20

*Primary Examiner*—R. E. Bagwill

*Attorney, Agent, or Firm*—Manford R. Haxton

[57] ABSTRACT

A hybrid tea rose variety having long stems bearing scarlet blooms of heavy substance (thick petals), long pointed buds, low fragrance, and good resistance to rose powdery mildew.

1 Drawing Figure

This present invention relates to a new and distinct variety of rose plant of the hybrid tea class which was originated by crossing the variety Flamingo (patent applied for) with an unnamed variety.

The primary objective of this breeding was to produce a new rose variety of the hybrid tea class bearing Scarlet flowers of improved petal substance, on long stems, and suitable for production of cut blooms. This objective was substantially achieved along with other desirable improvements as evidenced by the following unique combination of characteristics which are outstanding in the new variety and which distinguish it from its parents as well as from all other varieties of which I am aware:

1. Bud and flower color of scarlet equivalent to R.H.S. Red 46B;
2. Long, pointed buds;
3. Unusually heavy petals;
4. Long stems with normal thorns;
5. Good resistance to rose powdery mildew; and
6. Little or no fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Flamingo (patent applied for).

*Pollen parent.*—Unnamed variety.

Classification:

*Botanical.*—Rosa hybrid.

*Commercial.*—Hybrid tea.

FLOWER

Observations made from specimens grown in a greenhouse at Irvine, Calif. in March.

Blooming habit: Continuous.

Bud:

*Size.*—1½" when petals start to unfurl.

*Form.*—Pointed ovoid.

*Color.*—When sepals first divide, Near Red 46A; when half blown, upper side of petals, Near Red 46B; lower side of petals, Near Red 46C.

*Sepals.*—Color: Green 138B. Three appendaged sepals lightly appendaged. Two unappendaged sepals, hairy edge.

*Receptacle.*—Color: Green 138B. Shape: Funnel. Size: Large. Surface: Smooth.

*Peduncle.*—Length: Short. Surface: Smooth upper half, prickly lower half. Color: Light green. Strength: Stiff, erect.

*Opening.*—Spirally unfolding.

Open bloom:

*Size.*—Medium. Average open size 4½".

*Borne.*—Singly.

*Stems.*—Long to medium, strong.

*Form.*—When first open, high center. Permanence: Retains its form to the end, outer petal edges slightly curled.

*Petalage.*—Number of petals under normal conditions: Approximately 30.

*Color.*—Center of flower: Upper side of petals, Near Red 46B; reverse side of petals, Near Red 46C. Base of petals, small area Yellow 11A on both upper and lower petal surface. Major color: Red=R.H.S. Red 46B.

*Variegations.*—Occasional white vegetative streak in center of outer petal.

*Discoloration.*—General tonality at end of first day: No change in color. Third day: Near Red 46D.

*Fragrance.*—Slight.

Petals:

*Texture.*—Thick, rigid.

*Shape.*—Oval, base pointed.

*Form.*—Tips slightly recurved.

*Arrangement.*—Imbricated.

*Persistence.*—Drop off cleanly.

*Lastingness.*—On the plant, long. As cut flower, long.

Reproductive parts:

*Anthers.*—Large. Color: Yellow. Arrangement: Regular around styles.

*Filaments.*—Color: Reddish with yellow base.

*Pollen.*—Lemon yellow.

*Styles.*—Color: Reddish.

*Stigmas.*—Color: Greenish white.

PLANT

Form: Bush.

Growth: Vigorous, upright.

Foliage: Number of leaflets on normal mid-stem leaves: Usually 7, sometimes 5.

*Size.*—Medium.

*Quantity.*—Normal.

*Color.*—New foliage: Mostly light green, near R.H.S. Green 138B, slightly overcast with varying amounts of reddish pigment. Old foliage: Green 139A.

Leaflets:

*Shape.*—Broadly oval.

*Texture.*—Leathery.

*Edge.*—Serrated.

*Serration.*—Single, large.

*Petiole.*—Rachis: Color: Green. Underside: With prickles. Upperside: With small prickles.

*Stipules.*—Long, serrated near tips.

*Disease resistance.*—Resistant to mildew, under normal growing conditions at Irvine, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Hooked downward.

Small prickles:

*Quantity.*—On main stalks, none. On laterals, none.

We claim:

1. A new and distinct variety of rose plant of the hybrid tea class, substantially as herein shown and described, characterized particularly as to novelty by the unique combination of its long stems bearing scarlet blooms of heavy substance (thick petals), long pointed buds, low fragrance, and good resistance to rose powdery mildew.

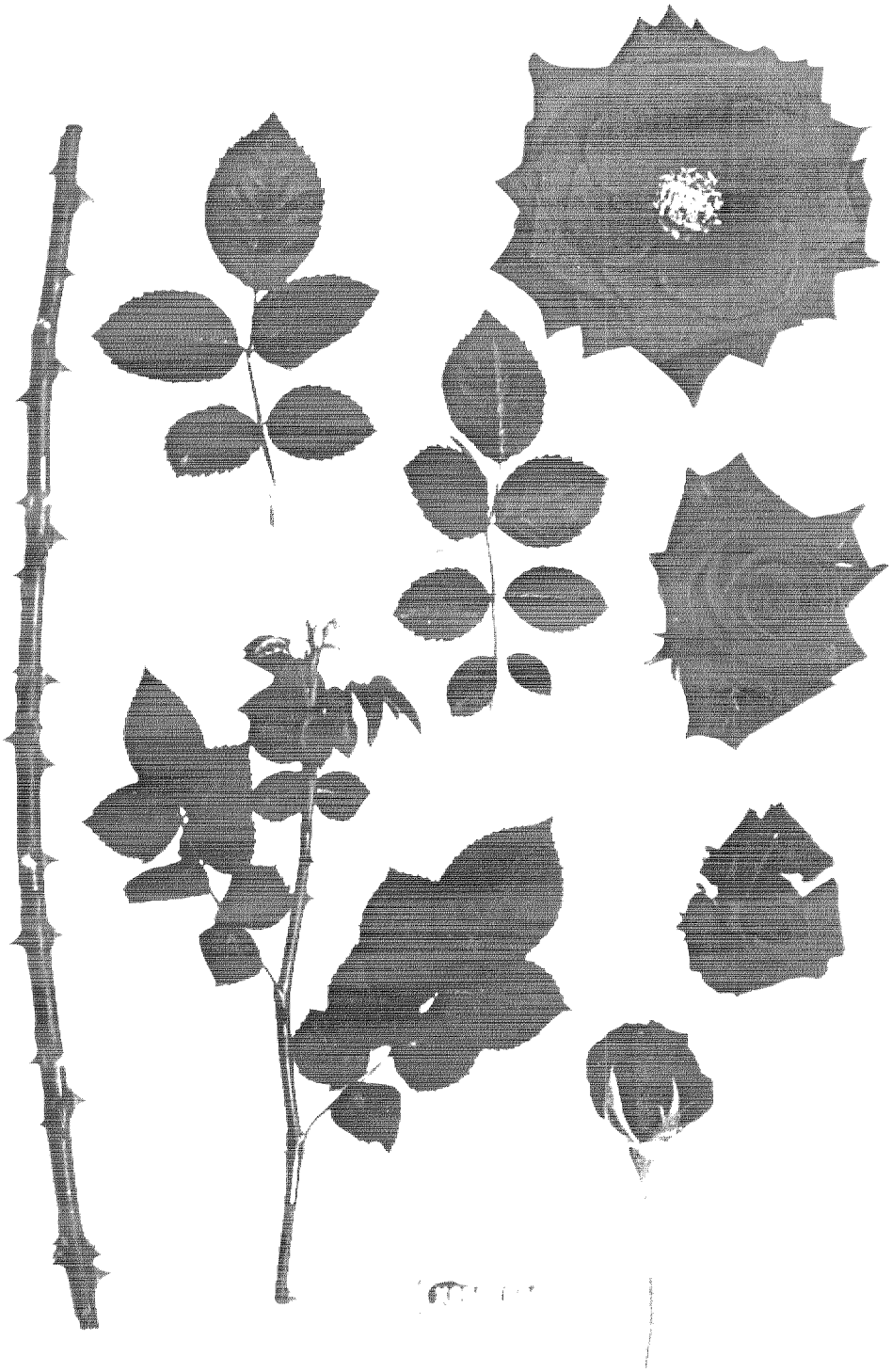

* * * * *